(12) United States Patent
Ellman et al.

(10) Patent No.: US 7,291,147 B1
(45) Date of Patent: Nov. 6, 2007

(54) FOREHEAD AND BROW LIFT BIPOLAR FORCEPS

(76) Inventors: Alan A. Ellman, 3333 Royal Ave., Oceanside, NY (US) 11572; Ion C. Garito, 3333 Royal Ave., Oceanside, NY (US) 11572

( * ) Notice: Subject to any disclaimer, the term of this patent is extended or adjusted under 35 U.S.C. 154(b) by 140 days.

(21) Appl. No.: 11/115,777

(22) Filed: Apr. 28, 2005

Related U.S. Application Data

(63) Continuation-in-part of application No. 10/770,198, filed on Feb. 2, 2004, now abandoned.

(51) Int. Cl.
*A61B 18/18* (2006.01)

(52) U.S. Cl. .............................. 606/41; 606/52; 128/898
(58) Field of Classification Search .................. 606/41, 606/45, 48–52; 128/898
See application file for complete search history.

(56) References Cited

U.S. PATENT DOCUMENTS 6,767,348 B2 * 7/2004 Nakada et al. ................ 606/46

* cited by examiner

*Primary Examiner*—Linda C. M. Dvorak
*Assistant Examiner*—Jacqueline Papapietro

(57) ABSTRACT

An electrosurgical electrode for performing an EFBL procedure comprises an elongated thin, forceps-shaped structure shaped to substantially match the curvature of the skull extending from the brow upward to a position at or above the hairline. The electrode terminates at a distal end in electrically-conductive spaced tips that are bare. The electrode is bipolar and is connected to electrosurgical apparatus capable of generating RF electrosurgical currents, preferably at a frequency of about 4 MHz. Bipolar forceps can also be provided at the end of a flexible tip handpiece, the forceps being manipulated by extending and retracting the forceps from the handpiece end.

2 Claims, 3 Drawing Sheets

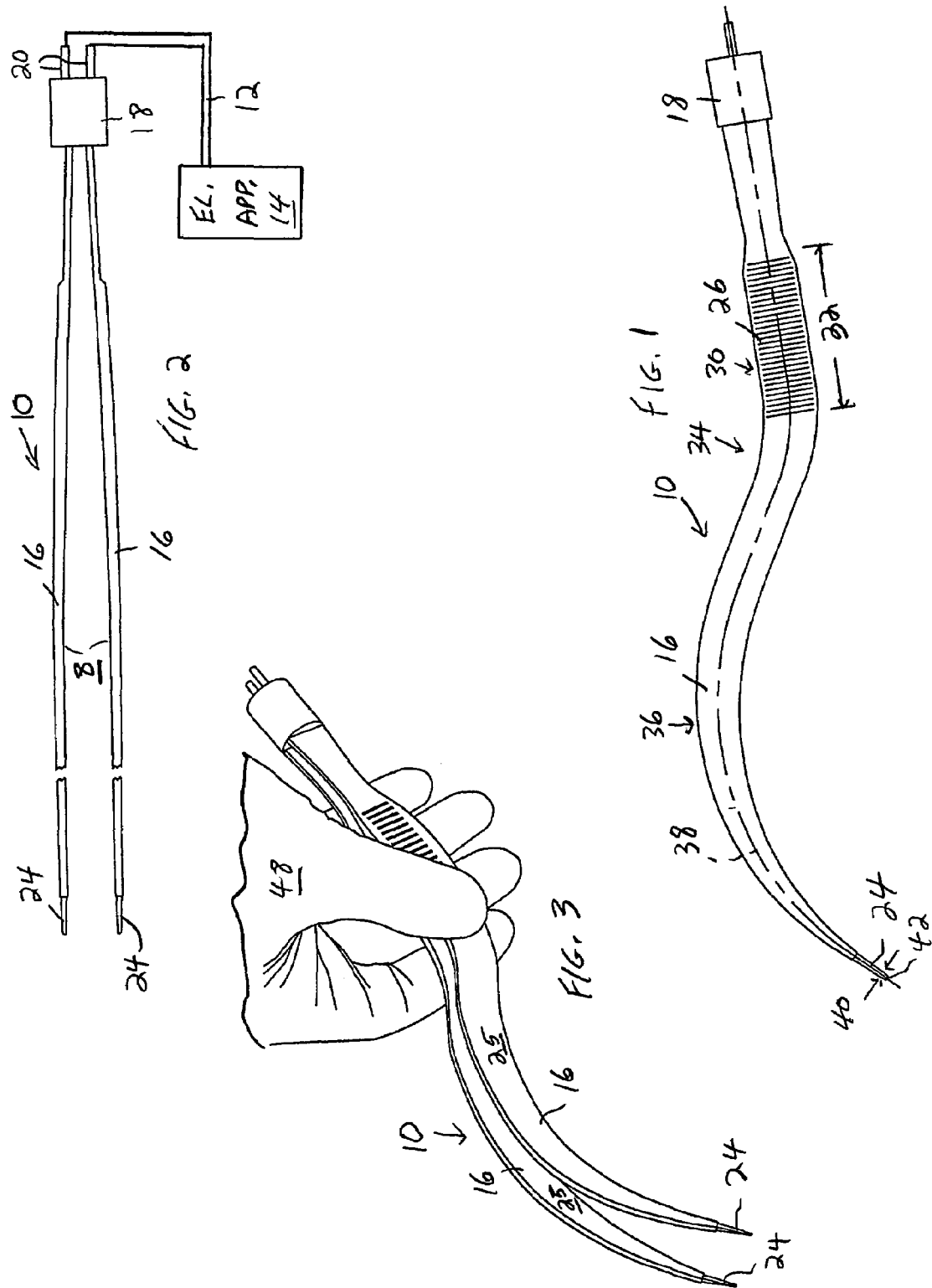

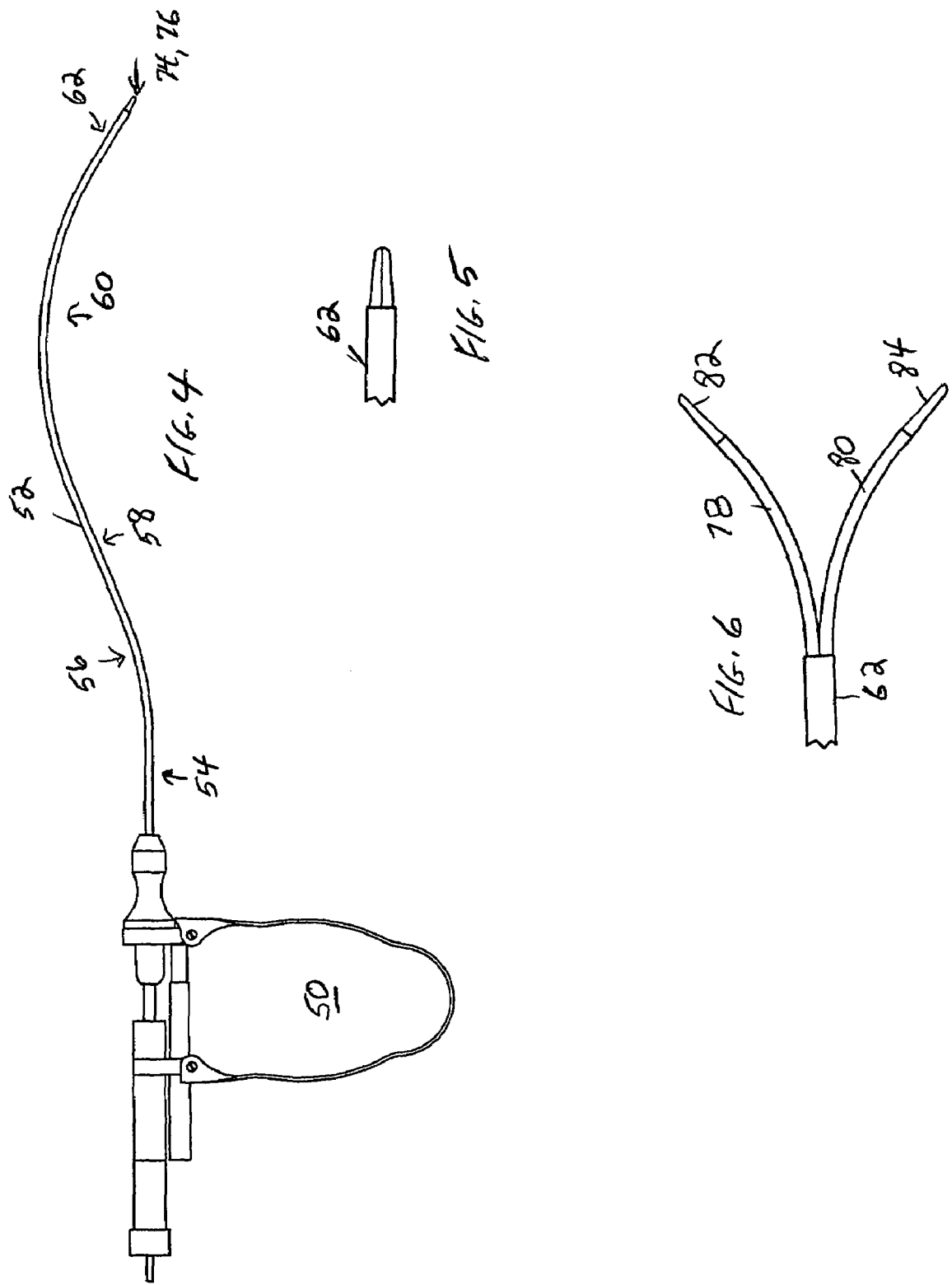

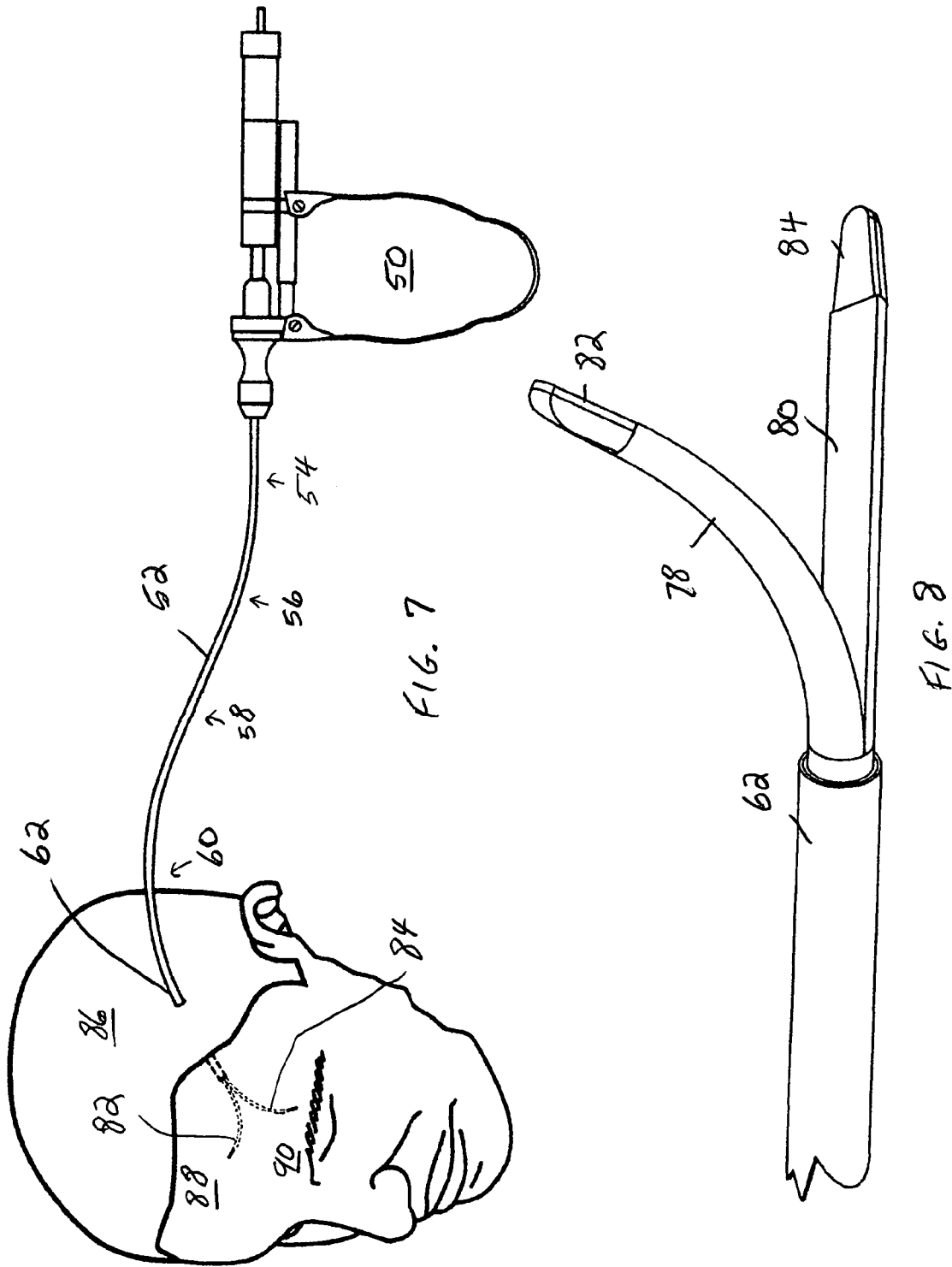

FOREHEAD AND BROW LIFT BIPOLAR FORCEPS

This application is a continuation-in-part of U.S. application Ser. No. 10/770,198, filed Feb. 2, 2004, now abandoned the contents of which are herein incorporated by reference.

This invention relates to an electrosurgical electrode, and in particular to a bipolar electrosurgical electrode for performing a surgical procedure known as an Endoscopic Forehead and Brow Lift (EFBL).

BACKGROUND OF THE INVENTION

In the EFBL procedure that is pertinent to this invention, via endoscopic visualization, a muscle extending over the brow and contributing to skin wrinkling due to excessive pulling forces on the skin is severed at least in part. Access to the muscle is obtained via a hole formed in the scalp at a position about three or so inches above the brow, and extending a probe with a through the hole and down via a tunnel forced between the scalp and the skull to the muscle to sever part or all of the same. If properly done, this should relieve the excessive pulling forces tending to smooth the forehead skin. See "Endoscopic Plastic Surgery", by Bostwick III, Eaves III, and Nahai, published by Quality Medical Publishing, Inc. of St. Louis Mo., 1995, Pgs. 166-170, the contents of which are hereby incorporated by reference, for a description of the procedure and how it works. See also "Opthalmic Plastic Surgery", ed. by Della Rocca, published by McGraw-Hill, of NYC, NY, 2002, Pgs. 209-222, the contents of which are hereby incorporated by reference, for another description of the procedure and how it works.

Scissors, monopolar electrosurgery (see our issued U.S. Pat. No. 6,306,135, the contents of which are hereby incorporated by reference), electrocautery and the CO2 laser have been used to perform the EFBL procedure. However, complications with these modalities have been reported, which include possible damage to the frontal branch of facial nerves which have sometimes resulted in eyebrow paralysis and have become a major worry among surgeons. A problem with these known procedures can be stray current or sparking coming from the monopolar electrosurgery or electrocautery, or laser jumping to the facial nerves or frontal branch nerves.

SUMMARY OF THE INVENTION

An object of the invention is a safer and more efficient method of dissection, ablation, and vaporization for use in carrying out an EFBL procedure.

A further object of the invention is a novel electrosurgical electrode for use in carrying out an EFBL procedure and which reduces or eliminates the problems of some of the known modalities.

Briefly stated, the use of bipolar radio-frequency (RF) energy reduces or eliminates these potential problems.

The use of bipolar electrosurgical energy has been previously suggested as a safer and more efficient method of dissection, ablation, and vaporization than traditional monopolar electrosurgery for other procedures. Many different kinds and shapes of bipolar electrodes have been proposed for use in different medical procedures. No one, so far as we know, has suggested the use of bipolar electrosurgical energy for use in EFBL, much less RF electrosurgical energy. It is speculated that a principal obstacle to bringing bipolar electrosurgical technology into the endoscopic forehead is the curvature of the skull and forehead. Getting instrumentation into this area and then, importantly, being able to manipulate the instrumentation after it has entered the area so that the EFBL procedure can be implemented is extremely difficult.

In accordance with a feature of the invention, a novel bipolar electrosurgical forceps is configured, extending from the brow upward to a position at or above the hairline, so that it matches the contours and curvature to the skull, forehead and mid-forehead. Because of its unique configuration, it can be advanced through 1-2 inch pretrichal small incisions in the forehead area. In addition, once positioned and through direct visualization, the bipolar forceps can be manipulated and squeezed by the surgeon to provide RF electrosurgical energy for dissection, ablation, vaporization, and most importantly, bipolar coagulation. In addition, these same properties of RF electrosurgical energy can be used if necessary to assist in positioning the forceps in the forehead or brow area most convenient for implementing the EFBL procedure.

As a result, the bipolar electrosurgical forceps of the invention offers the cosmetic surgeon doing endoscopic forehead and brow lift a safe surgical alternative to scissors, CO2 lasers and traditional monopolar electrosurgery and electrocautery.

In a preferred embodiment, the curved bipolar forceps terminates at a distal end in a two laterally spaced bare tips. The forceps body itself comprises separate, electrically-insulated arms or tines, preferably of spring metal, covered with an electrically-insulating coating so that the electrosurgical currents are concentrated at the bare tips of the tines. The natural resilience of the forceps body causes the tines to occupy a normally-open position, and gripping areas are provided at their proximal end for the surgeon to manipulate the tines toward their closed position. The proximal end terminates in a connector that can be connected by a cable to conventional electrosurgical apparatus.

In another preferred embodiment, the curved bipolar forceps can be integrated into a known flexible tip bipolar electrode characterized by a gun-type handle that when squeezed projects active electrodes from a narrow tubular extension at its distal end, the construction being such that the exended forceps ends, normally occupying their rest closed position inside the narrow tubular extension, open and occupy their normally-open position when extended by squeezing of the handle, but when the pressure on the handle is relaxed, the forceps ends retract while simultaneously closing toward one another in order to resume their rest closed position inside the narrow tubular extension. The basic construction but without the critical curvature that allows the instrument to be used in the EFBL procedure is described in our U.S. Pat. No. 6,231,571, the contents of which are hereby incorporated by reference.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a side view of one form of an electrode in accordance with the invention;

FIG. 2 is a top view of the electrode of FIG. 1 shown connected to electrosurgical apparatus;

FIG. 3 is a perspective view showing the electrode of FIG. 1 held by a surgeon's hand in operative position;

FIG. 4 is a side view of a modified form of an electrode according to the invention;

FIG. 5 is an enlarged view of the active tip of the electrode of FIG. 4 in its retracted position;

FIG. 6 is a view of the active tip of the electrode of FIG. 4 in its extended position from its housing;

FIG. 7 is a perspective view of the FIG. 4 embodiment used in an EFBL procedure;

FIG. 8 is an enlarged perspective view of the working electrode end of FIG. 7 when the electrode is in its extended position.

DETAILED DESCRIPTION OF THE PREFERRED EMBODIMENTS

FIG. 1 is a side view of one form of an electrode 10 in accordance with the invention. FIG. 2 shows the electrode of FIG. 1 connected by way of a cable 12 to a suitable source 14 of electrosurgical currents. Any electrosurgical apparatus 14 capable of generating RF bipolar electrosurgical currents can be used. A preferred apparatus is available from Ellman International of Hewlett, N.Y. as Model IEC50, IEC 100 or RADIOLASE.

The electrode 10 shown in FIGS. 1 and 2 comprises a bipolar forceps body structure 8, sometimes known as pincers or tongs in the medical arts, comprising spaced elongated tines or arms 16 mounted to and supported by a connector 18 having two prongs 20. The arms 16 are constituted of an electrically conductive material, preferably of spring metal such as stainless steel or brass, and are electrically-insulated from one another. The bipolar forceps terminates at a distal end in a two laterally spaced bare tips 24. The forceps body 8 itself is covered with an electrically-insulating coating 25 so that the electrosurgical currents are concentrated at the bare tips 24. The natural resilience of the forceps body 8 causes the tips 24 to occupy a normally-open position as shown in FIG. 1, and gripping areas 26, for example grooves or knurls, are provided along the sides at their proximal end for the surgeon to manipulate the bare tips 24 toward their closed position.

The curved shape of the front part of the forceps is critical to achieving the objectives of the invention. As explained and illustrated in U.S. Pat. No. 6,306,135, for carrying out the EFBL procedure in accordance with the present invention, the forceps, bare tips first, are advanced through small incisions in the forehead area and are shaped to follow the contour and curvature of the skull, forehead, and mid-forehead to reach the brow area and at that area perform the necessary dissection for the cosmetic surgery desired. For best results in accordance with the present invention, a double curvature proves to be the most desirable. Specifically, the handle section 30 can be straight over a length 32 of about 2-3 inches, followed by a first upwardly-curved section 34 with a radius of about 1.5-2.2 inches, in turn followed by a second downwardly curved section 36 with a radius of about 2.8-3.2 inches, eventually reaching the bare tips 24. The longitudinal axis is represented by the center line 38, and the various sections have the following approximate lengths measured along the center line 38: handle section 30 about 2-3 inches, first curved section 34 about 1-1.8 inches, second curved section 36 about 4-5.5 inches. The more important curvature is the second curved section 36 as that is the part of the electrode that is actually inserted under the scalp tissue of the patient. The width of the bare tips indicated at 40 is about 0.06-0.12 inches and the point 42 is not sharp but can have a radius of about 0.02-0.03 inches.

Whereas in U.S. Pat. No. 6,306,135 the blunt front end of the monopolar electrode could be used for blunt dissection, in the present invention, while some dissection is possible with the bare tips 24, the surgeon while introducing the electrode 10 can manipulate the forceps tines and also use his conventional foot pedal to activate the electrosurgical apparatus generating electrosurgical currents between the bare tips 24 which will help cut dissect, ablate or vaporize tissue while the forceps electrode is being navigated to the brow area through direct visualization via the usual endoscope.

The important benefit of the invention is that the electrosurgical currents are confined to the small area between the bare tips 24, so the likelihood of stray current or sparking damaging facial or frontal branch nerves is minimized. Moreover, while at the operative site, the surgeon can easily manipulate and squeeze the forceps ends to reach the tissue to be treated. Another important benefit is that bipolar coagulation of any bleeders present is easily achieved by gripping the bleeders between the squeezed bare tips and activating the electrosurgical apparatus.

FIG. 3 illustrates the bipolar forceps 10 of the invention in the hand of a surgeon 48.

FIGS. 4-8 illustrate a modified bipolar forceps employing the flexible tip construction described in U.S. Pat. No. 6,231,571. That patent shows the use of a trigger operated forceps in which the active electrode, unipolar or bipolar, is projected out of the end of a tubular member serving as a housing upon squeezing a hand grip. The present invention derives an embodiment based on that construction as illustrated in FIG. 20 of the patent. The latter shows a scissor electrode which when projected out of its tubular housing opens up the scissor jaws, and when the user relaxes his or her grip, the scissors retracts, but due to the outward bends in the scissors—which in its out position has an outside diameter that exceeds the housing opening—during the retraction process the scissor jaws are moved toward one another and can then cut intervening tissue.

The present invention takes advantage of that principle. In FIG. 4, the handle end 50 is similar to that shown in FIG. 18 of U.S. Pat. No. 6,231,571 and so need not be repeated here. The tubular housing 52 is shaped to follow the contours and curvature of the skull 86, forehead 88, and mid-forehead to reach the brow area 90 of the patient for implementing the EFBL procedure (see FIG. 7). Following a first straight section 54, a second curved section 56 that turns into a third straight section 58, followed by a fourth curved section 60, in turn followed by a final straight section 62. The relative dimensions can be approximately the same as those given above for the FIG. 1 embodiment. It will be understood that the dimensions given above are preferred for the average adult patient. However, while preferred, small variations are possible for use with smaller or larger headed patients. In general, however, the double curvature—similar to a kind of S-shape—is preferred, the S-shape being indicated in FIG. 1 by curved sections 34 and 36, the S-shape being indicated in FIG. 4 by curved sections 56 and 60. It will be understood that the FIG. 4 embodiment is bipolar with each arm or tine insulated by suitable means such as the dual lumens of the patent. In the latter case, the dual lumens can be placed one above the other or side by side and the distal projecting ends 74, 76 are electrically-insulated and oppositely curved to form bent sections 78, 80 and constituted, preferably, of a memory metal as described in U.S. Pat. No. 6,231,571 so that they tend to spread apart when the handle 50 is squeezed as shown in FIG. 6 and when projected from their respective lumens at the housing end 62. The active electrode tips 82, 84, otherwise insulated from one another, are bare for applying bipolar electrosurgical currents. When the user's grip on the handle 50 relaxes and the projected ends 78, 80 begin to retract, the smaller-diameter housing (lumens) 62 forces the projected ends 78, 80 toward one another allowing the forceps tips 82, 84 to grasp tissue regions for appropriate treatment as described above. It will also be understood that a construction similar to the scissors as illustrated in FIG. 20 of the patent can be substituted to provide opening and closing of the forceps tips as the active ends are extended and retracted from their housing.

As one example of an EFBL procedure, not to be limiting, the scalp is perforated above the brow and an endoscope probe inserted so that the surgeon can visualize the progress of the procedure. The blunt edge of the endoscope probe can sometimes be used with blunt dissection to move tissue to provide a space between the scalp and skull within which the electrode will be inserted and that will allow the surgeon to visualize the actions of the inserted electrode. Then the electrode 10 is inserted from above, typically by way of a lateral incision, and advanced down in the space between the scalp and the skull toward the brow 90. With or without electrode activation, as the surgeon advances the electrode 10, the tissues binding the scalp to the skull are displaced. This is continued until the muscle or other tissue to be dissected, ablated or vaporized is reached, approximately 3-6 inches below the initial perforation. Then the electrosurgical apparatus 14 is activated while the surgeon manipulates the forceps tines with its bare tips 24 to sever muscle tissue or coagulate bleeders by the emitted electrosurgical currents. The electrode 10 may then be withdrawn and the rest of the normal procedure followed.

Summarizing, in the invention the curved forceps are in a tubular housing 52. The forceps are extended and retracted with respect to the housing 52 held by the surgeon. Note in FIGS. 4-6 of applicants' drawing that the forceps arms 78, 80 are together within the outer housing 52 when they are in the retracted position illustrated in FIGS. 4 and 5. The curved tube with the retracted forceps can then be inserted into the brow of the patient as illustrated in the referenced '571 patent and in FIG. 7. Then, when the curved structure has reached its inserted position, then the forceps end is extended from the outer housing 52 by squeezing the handle 50 and the forceps open to embrace tissue that needs treatment. As the doctor releases the handle pressure, the forceps ends come together as they retract into the outer tube which can remain stationary causing the ends to grasp any tissue positioned between the ends, and then application of electrosurgical currents will cause the surgical action desired.

The insulating coatings 25 will prevent accidental touching of patient tissue by the electrode sides, so that the electrosurgical currents are localized between the bare electrode ends 24.

The apparatus used in the procedure preferably generates electrosurgical currents with an RF frequency, about 4 MHz being preferred.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A procedure for performing an electrosurgical Endoscopic Forehead and Brow Lift procedure on the forehead of a human patient; comprising the steps:
    A) providing an electrosurgical apparatus for generating electrosurgical currents to a handpiece connected to the apparatus and comprising:
        (a) an elongated tubular housing containing an extendable structure and provided at a proximal end with means for extending and retracting the extendable structure from a distal end of the housing;
        (b) the housing comprising, in order starting from the proximal end, at least a straight section and a curved section,
        (c) the curved section having a shape substantially matching the skull and forehead of the patient to undergo the electrosurgical Endoscopic Forehead and Brow Lift procedure, whereby the housing can be inserted into the skull of the patient to undergo the electrosurgical procedure;
        (d) the extendable structure comprising: a bipolar forceps structure comprising:
            (i) a handle and electrically-insulated arms provided at a distal end with electrically-conductive tips serving as active electrodes from which the electrosurgical currents can emanate when the handpiece is connected to the electrosurgical apparatus,
            (ii) the forceps structure being configured so as to spread apart with respect to the housing separating the electrically-conductive tips when in its extended position but forcing them toward one another with respect to the housing when returning the forceps structure to its retracted position, such that the coming together of the electrically-conductive tips can be used to dissect, ablate, vaporize or coagulate tissue when the electrosurgical apparatus is activated;
            (iii) the electrically-conductive tips being bare so as to allow the electrosurgical currents to enter contacted tissue when the electrosurgical apparatus is activated,
    B) inserting the electrically-conductive tips from above the brow into the space formed between the scalp and the skull until reaching the muscle tissue extending over the brow;
    C) squeezing the handle to extend the electrodes and spread them around the muscle tissue to be treated,
    D) releasing the handle to close the electrodes around the muscle tissue to be treated, and
    E) activating the electrosurgical apparatus and treating the muscle tissue with the electrosurgical currents from the electrically-conductive tips.

2. A procedure for performing an electrosurgical Endoscopic Forehead and Brow Lift procedure on the forehead of a human patient as claimed in claim 1, wherein the electrosurgical apparatus generates the electrosurgical currents with a frequency in the megacycle range.

* * * * *